(12) United States Patent
Kabakov et al.

(10) Patent No.: US 9,168,022 B2
(45) Date of Patent: Oct. 27, 2015

(54) ABDOMINAL SONAR SYSTEM AND APPARATUS

(75) Inventors: Serguei Kabakov, Savage, MD (US); Steven M. Falk, Baltimore, MD (US); Karsten A. Russell-wood, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 1081 days.

(21) Appl. No.: 12/986,778

(22) Filed: Jan. 7, 2011

(65) Prior Publication Data

US 2012/0179046 A1    Jul. 12, 2012

(51) Int. Cl.
*A61B 8/00* (2006.01)
*A61B 8/08* (2006.01)
(Continued)

(52) U.S. Cl.
CPC ........... *A61B 8/0866* (2013.01); *A61B 5/02411* (2013.01); *A61B 8/02* (2013.01); *A61B 8/4227* (2013.01); *A61B 8/4472* (2013.01); *A61B 8/4477* (2013.01)

(58) Field of Classification Search
None
See application file for complete search history.

(56) References Cited

U.S. PATENT DOCUMENTS 3,606,879 A * 9/1971 Estes .............................. 600/437
RE28,990 E 10/1976 Hon et al.

(Continued)

FOREIGN PATENT DOCUMENTS

CN 202069604 U 12/2011
WO WO 9748501 * 6/1997 ............... A61B 5/00

(Continued)

OTHER PUBLICATIONS

Breeveld-Dwarkasing, et al; Cervical Dilatation Related to Uterine Electromyographic Activity and Endocrinological Changes During Prostaglandin F2α-Induced Parturition in Cows; Biology of Reproduction, vol. 68, (2003), pp. 536-542.

(Continued)

*Primary Examiner* — Unsu Jung
*Assistant Examiner* — Joseph M Santos Rodriguez
(74) *Attorney, Agent, or Firm* — Andrus Intellectual Property Law, LLP (57) ABSTRACT

An abdominal sonar includes an ultrasound transducer array with a plurality of ultrasound transducers. The abdominal sonar further includes at least one additional ultrasound transducer. A digital signal processor is communicatively connected to the plurality of ultrasound transducers and the at least one additional ultrasound transducer. The digital signal processor individually operates the plurality of ultrasound transducers and the at least one additional ultrasound transducer. The digital signal processor receives reflected ultrasound signals back from each of the plurality of ultrasound transducers and the at least one additional ultrasound transducer and converts the received reflected ultrasound signals into an audio signal. A system for monitoring a pregnancy includes an ultrasound transducer array and at least one additional ultrasound transducer. A digital signal processor is communicatively connected to the ultrasound transducer array and the at least one ultrasound transducer. The digital signal processor converts received raw fetal heart and uterine activity waveforms into an audio signal. A wireless transmitter broadcasts the received audio signal. A wireless receiver receives the broadcast audio signal. A patient monitor extracts the raw fetal heart and uterine activity waveforms from the audio signal and processes the waveforms to obtain an indication of fetal heart rate and an indication of uterine activity.

15 Claims, 4 Drawing Sheets

(51) Int. Cl.
*A61B 5/024* (2006.01)
*A61B 8/02* (2006.01)

(56) References Cited

U.S. PATENT DOCUMENTS

| | | | |
|---|---|---|---|
| 4,781,200 A * | 11/1988 | Baker | 600/483 |
| 4,966,152 A | 10/1990 | Gang et al. | |
| 5,257,627 A | 11/1993 | Rapoport | |
| 5,265,613 A | 11/1993 | Feldman et al. | |
| 5,596,993 A * | 1/1997 | Oriol et al. | 600/511 |
| 5,640,960 A * | 6/1997 | Jones et al. | 600/453 |
| 6,093,151 A | 7/2000 | Shine et al. | |
| 6,151,520 A | 11/2000 | Combs | |
| 6,171,263 B1 | 1/2001 | Sullivan | |
| 6,292,679 B1 | 9/2001 | Sheard | |
| 6,416,471 B1 | 7/2002 | Kumar et al. | |
| 6,816,744 B2 | 11/2004 | Garfield et al. | |
| 6,843,771 B2 | 1/2005 | Lo et al. | |
| 6,863,653 B1 | 3/2005 | Zanelli et al. | |
| 6,918,875 B2 * | 7/2005 | Moriya et al. | 600/443 |
| 7,207,941 B2 * | 4/2007 | Sharf | 600/438 |
| 7,336,985 B2 | 2/2008 | Wallace et al. | |
| 7,527,597 B2 * | 5/2009 | Sandler et al. | 600/504 |
| 7,758,522 B2 | 7/2010 | Pandit | |
| 2005/0075565 A1 | 4/2005 | Satoh | |
| 2008/0208057 A1 * | 8/2008 | Hoctor et al. | 600/453 |
| 2009/0143650 A1 | 6/2009 | Guion-Johnson et al. | |

FOREIGN PATENT DOCUMENTS

| | | | |
|---|---|---|---|
| WO | 0178577 | 10/2001 | |
| WO | 02096288 | 12/2002 | |
| WO | 2004086085 A1 | 10/2004 | |
| WO | 2005025419 A1 | 3/2005 | |
| WO | WO 2008146201 A2 * | 12/2008 | A61B 5/00 |
| WO | 2009013701 A2 | 1/2009 | |
| WO | 2012142493 A2 | 10/2012 | |

OTHER PUBLICATIONS van Engelen, E. et al; EMG activity of the muscular and stromal layer of the cervix in relation to EMG activity of the myometrium and cervical dilatation of PGF2α induced parturition in the cow; Theriogenology, vol. 67, (2007), pp. 1158-1167.
Corometrics® 170 Series; Operator's Manual; Manual P/N 2002023-001 Rev.D; GE Medical Systems Information Technologies.
Search Report from corresponding GB Application No. 1200129.3 May 4, 2012.
Unofficial translation of NL Search Report from NL Application No. 2008076 dated Dec. 17, 2013.

* cited by examiner

ABDOMINAL SONAR SYSTEM AND APPARATUS

BACKGROUND

The current disclosure is related to the field of physiological monitoring of a pregnant patient. More specifically, the present disclosure relates to the use of ultrasound in physiological monitor of a pregnant patient.

External fetal monitoring provides valuable information regarding the physiological condition of both a pregnant mother and a fetus during labor prior to delivery. Currently, a tocodynamometer is used to detect the uterine activity, or contraction, of the mother, while an ultrasound transducer is used to detect fetal heart rate (FHR). The use of two different modalities to monitor these physiological parameters requires two devices to be attached to the mother. This results in redundancy of components and decreases the mobility and/or comfort of the mother during labor.

BRIEF DISCLOSURE

An abdominal sonar for use with a pregnant patient includes an ultrasound transducer array. The ultrasound transducer array includes a plurality of ultrasound transducers. The abdominal sonar further includes at least one additional ultrasound transducer. A digital signal processor is communicatively connected to the plurality of ultrasound transducers of the ultrasound transducer array and is communicatively connected to the at least one additional ultrasound transducer. The digital signal processor individually operates the plurality of ultrasound transducers and the at least one additional ultrasound transducer to produce an ultrasound signal, receives reflected ultrasound signals back from each of the plurality of ultrasound transducers and the at least one additional ultrasound transducer, and converts the received reflected ultrasound signals into a low-frequency audio signal. A wireless transmitter is communicatively connected to the digital signal processor. The wireless transmitter receives the audio signal from the digital signal processor and broadcasts the received audio signal.

A system for monitoring a pregnancy includes an ultrasound transducer array comprising a plurality of ultrasound transducers and at least one additional ultrasound transducer. A digital signal processor is communicatively connected to the plurality of ultrasound transducers of the ultrasound transducer array and is communicatively connected to the at least one additional ultrasound transducer. The digital signal processor individually operates the plurality of ultrasound transducers and the at least one additional ultrasound transducer to produce an ultrasound signal. The digital signal processor receives the reflected ultrasound signals back from each of the plurality of ultrasound transducers and the at least one additional ultrasound transducer. The digital signal processor converts the received reflected ultrasound signals into a low-frequency audio signal. A wireless transmitter is communicatively connected to the digital signal processor. The wireless transmitter receives the audio signal from the digital signal processor and broadcasts the received audio signal. A wireless receiver is communicatively connected to the wireless transmitter such that the wireless receiver receives the broadcast audio signal. A patient monitor is communicatively connected to the wireless receiver, the patient monitor extracts the received reflected ultrasound signals from the analog audio signal and processes the received reflected ultrasound signals to obtain an indication of fetal heart rate and an indication of uterine activity.

A system for monitoring a pregnancy includes an ultrasound transducer array including a plurality of ultrasound transducers and at least one additional ultrasound transducer. A digital signal processor is communicatively connected to the plurality of ultrasound transducers of the ultrasound transducer array and to the at least one additional ultrasound transducer. The digital signal processor operates the plurality of ultrasound transducers to produce ultrasound tone signals. The digital signal processor operates the at least one additional ultrasound transducer to produce an ultrasound chirp signal. The digital signal processor receives reflected ultrasound tone signals back from each of the plurality of ultrasound transducers and receives a reflected ultrasound chirp signal from the at least one additional ultrasound transducer. The digital signal processor combines the received reflected ultrasound tone signals and received reflected ultrasound chirp signal into a low-frequency audio signal. A wireless transmitter is communicatively connected to the digital signal processor. The wireless transmitter receives the analog audio signal from the digital signal processor and broadcasts the received audio signal. A wireless receiver is communicatively connected to the wireless transmitter such that the wireless receiver receives the broadcast audio signal. A patient monitor is communicatively connected to the wireless receiver. The patient monitor extracts the received reflected ultrasound tone signals and the received reflected ultrasound chirp signal from the analog audio signal. The patient monitor processes the received reflected ultrasound tone signals to obtain an indication of fetal heart rate. The patient monitor processes the received reflected ultrasound chirp signal to obtain an indication of uterine activity.

DETAILED DISCLOSURE

Figure 1:
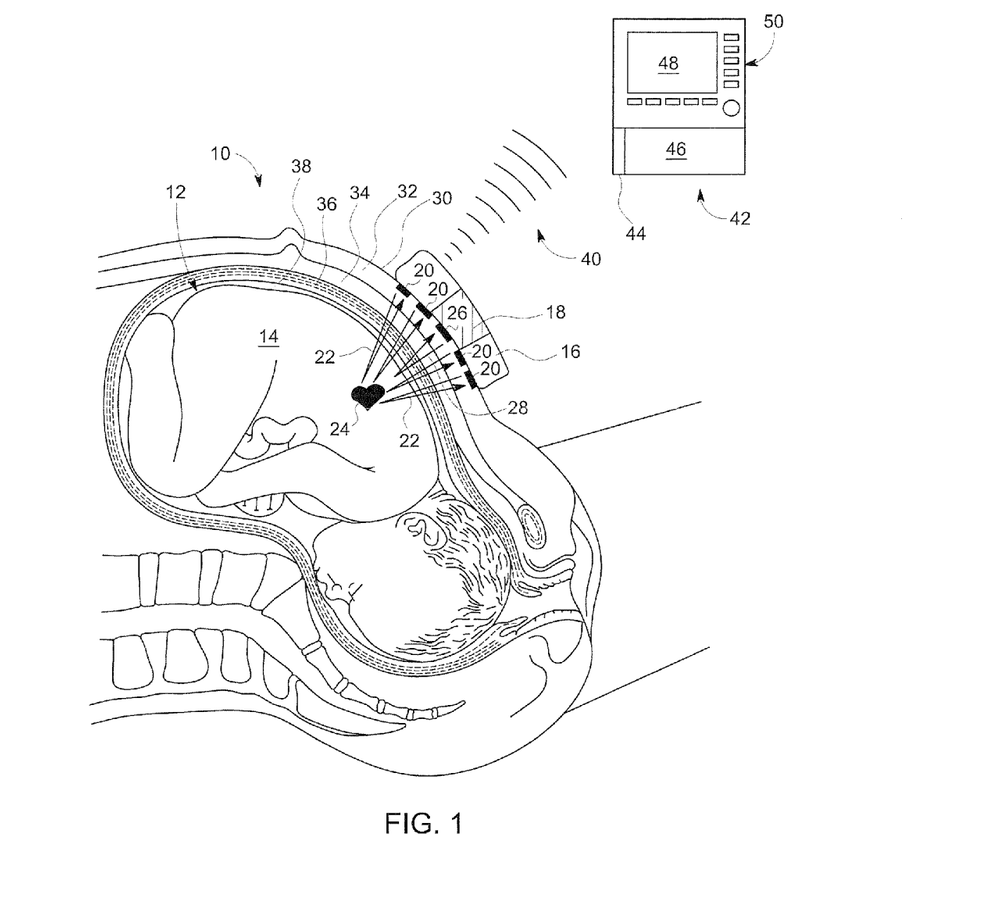
FIG. 1 is a cutaway view of a uterus and fetus with an embodiment of the abdominal sonar.

FIG. 1 is a cross sectional view of a womb 12 of a mother 10 within which a fetus 14 is disposed. The mother 10 is typically in labor or experiencing uterine contractions in preparation for labor and delivery. An abdominal sonar 16, as disclosed herein, is secured to the abdomen of the mother 10. The abdominal sonar 16 is secured to the mother 10 in one embodiment using an elastomeric band 18. The elastomeric band 18 secures around the mother 10 to hold the abdominal sonar 16 in contact with the mother 10. It is recognized that in alternative embodiments, the abdominal sonar 16 may be secured to the mother 10 in a variety of alternative manners, including the use of a biocompatible adhesive.

Additionally, in some embodiments, a gel or other ultrasound conductive substance (not depicted) is applied to the mother 10 to improve the ultrasound interface between the abdominal sonar 16 and the mother 10. The abdominal sonar 16 includes an ultrasound transducer array that includes a plurality of ultrasound transducers 20. The ultrasound array transducers 20 operate to produce ultrasound single tone pulse signals 22 that are directed towards a heart 24 of the fetus 14. The ultrasound tone signals 22 reflect off of the heart 24 of the fetus 14 and return to the ultrasound array transducers 20.

The abdominal sonar 16 further includes at least one additional ultrasound transducer 26. The additional ultrasound transducer 26 produces an ultrasound chirp signal 28. The ultrasound chirp signal 28 passes through a variety of layers of tissue of the mother 10. These layers include the mother's skin 30, subcutaneous fat 32, abdominal muscle 34, uterine wall 36, and amniotic fluid 38. In additional embodiments, the ultrasound chirp signal 28 passes into the fetus 14 as well. The ultrasound chirp signal 28 is reflected each time that the ultrasound chirp signal 28 passes through a material of a different density. Therefore, a plurality of echoes are returned to the additional ultrasound transducer 26 as the ultrasound chirp signal 28 passes through each layer highlighted above and finally into the amniotic fluid 38 or the fetus 14, depending upon the positioning of the fetus 14 within the womb 12.

As will be described in further detail herein, the abdominal sonar 16 processes the returned ultrasound tone signals 22 and the returned ultrasound chirp signal 28 and converts these ultrasound signals into an analog audio signal. Exemplarily, the audio signal is between 1 KHz and 10 KHz. The analog audio signal is wirelessly broadcast 40 from the abdominal sonar 16 by a wireless transmitter (not depicted).

It is understood that while an analog audio signal is described in detail herein, in alternative embodiments, the signal is a digital audio signal.

The wireless broadcast 40 is received by a patient monitor 42 that includes a wireless receiver 44. It is to be understood that the wireless receiver 44 and the wireless transmitter (not depicted) may be any of a compatible pair of wireless communication devices, that include, but are not limited to radio frequency (RF) exemplified by a wireless communication device operating according to the BLUETOOTH wireless communication protocol, infrared (IR), or other optical communication. It is further recognized that other wireless communication systems may also be considered to be within the scope of the disclosure.

The patient monitor 42 further includes a digital signal processor 46 that receives and processes the audio signal in order to determine the uterine activity of the mother 10 and the fetal heart rate. The operation of the digital signal processor 46 will be described in further detail herein.

The patient monitor 42 further includes a graphical display 48 and an input device 50. The graphical display 48 is operated by the digital signal processor 46 in order to present graphical representations of the determined uterine activity and fetal heart rate. The input device 50 in embodiments is a keyboard data wheel, soft key, touch screen interface, or other data input devices as recognized by one of ordinary skill in the art that is used by the clinician to enter, select, and manipulate data in conjunction with the digital signal processor 46.

Figure 2A:
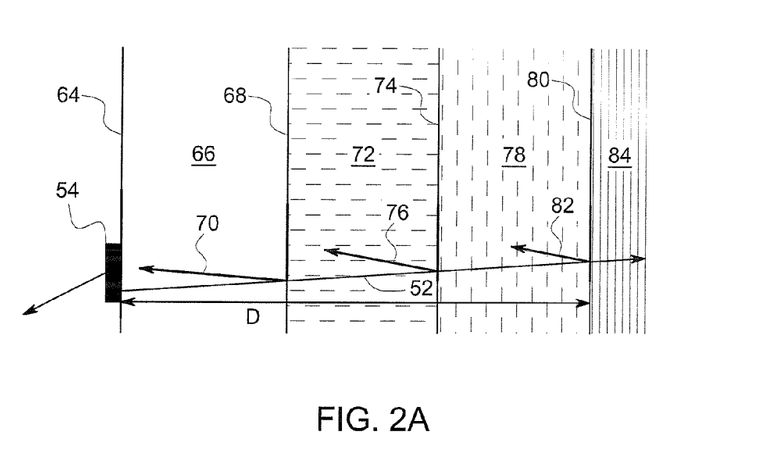
FIG. 2A is a close up view of a cross section of a pregnant mother's abdominal wall.
Figure 2B:
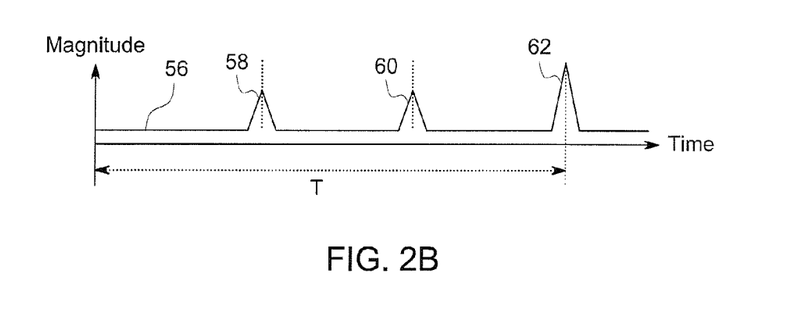
FIG. 2B is an exemplary embodiment of a received reflected ultrasound chirp signal.

FIGS. 2A and 2B diagrammatically depict the transmission of an ultrasound chirp signal through the tissue of a mother. An ultrasound chirp signal is a signal that increases in frequency over time. A feature of an ultrasound chirp signal is that the chirp signal will produce an echo back to the ultrasound transducer when the chirp signal passes between an interface of two materials of different density.

FIG. 2A depicts the physical progression of the chirp signal 52 produced by the additional ultrasound transducer 26. FIG. 2B depicts a correlation signal 56 representative of the magnitude of the correlation between the original chirp signal and the received chirp echoes. The correlation signal 56 exhibits a plurality of peaks 58, 60, 62 as will be described in further detail herein. FIG. 2A and FIG. 2B are aligned such as to show the relationship between the physical dimension in FIG. 2A and the temporal dimension in FIG. 2B.

As noted above, the ultrasound transducer 54 is secured to the mother's skin 64. The ultrasound transducer 54 is exemplarily the uterine activity ultrasound transducer 26 (FIG. 1). The ultrasound transducer 54 produces an ultrasound chirp signal 52 that passes through the mother's skin 64 and the layer of subcutaneous fat 66. At interface 68 between the subcutaneous fat 66 and the abdominal muscle 72, an echo 70 is returned to the ultrasound transducer 54. This returned echo 70 coincides with the peak 58 in the correlation signal 56. The ultrasound chirp signal 52 continues to pass through the abdominal muscle 72 and at the interface 74 between the abdominal muscles and the uterine wall 78, an echo 76 is returned to the ultrasound transducer 54. This returned echo 76 coincides with the peak 60 in the correlation signal 56.

The ultrasound chirp signal 52 continues through the uterine wall 78 and at an interface 80 between the uterine wall and the amniotic fluid 84, a still further echo 82 is returned to the ultrasound transducer 54. Due to a large degree in density change between the uterine wall 78 and the amniotic fluid 84, a peak 62 in the correlation signal 56 (FIG. 2B) is larger than the peaks 58, 60 of the previous tissue interfaces.

As noted above, the correlation signal 56 represents the magnitude of correlation between the original chirp pulse and the returned echoes. As the tissue interfaces 68, 74, 80 produce stronger return echoes than the surrounding tissues, the correlation of these echoes to the original chirp signal are the strongest, forming the respective identified peaks 58, 60, and 62. It is recognized that in embodiments, the chirp signal and the reflected echoes attenuate as the signals progress through the patient. Therefore, the correlation signal 56 may be a normalized correlation which accounts for this attenuation.

It is to be noted that due to the positioning of the fetus within the mother, the amniotic fluid 84 in FIG. 2A may alternatively be the fetus itself or an air bubble. Differences in this interface 80 may result in one of the previous interfaces 68, 74 resulting in the correlation peak 58, 60 of the greatest magnitude. In these embodiments, one of the other correlation peaks 58, 60 may be monitored.

As can be seen from a comparison between FIGS. 2A and 2B, the distance between the patient's skin 64 and an interior side of the uterine wall 78 is proportional to the time between the start of the chirp signal 52 and the returned maximum echo peak 62. Therefore, the peak 62 that coincides with the uterine wall/amniotic fluid interface 80 is related to the distance D traveled by the ultrasound chirp signal, and can be derived from the time delay to the peak 62. A contraction by the mother will decrease the distance traveled by the ultrasound chirp signal 52, which will result in a decrease in the time until the returned echo peaks 62. Furthermore, the intensity of the contraction can be monitored as a function of the change in the distance D as a stronger contraction will result in a greater decrease in the distances between the layers of the mother's tissue, and a shorter time until echo peak 62. The change in distance is often due, at least in part, to compression of the subcutaneous fat layer 66 by the contractions.

Figure 3:
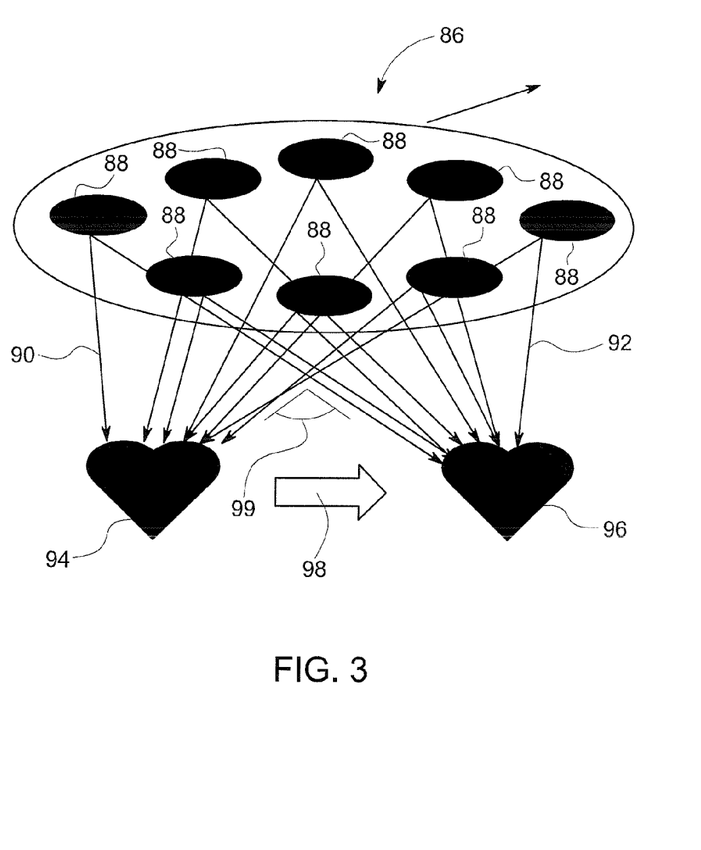
FIG. 3 depicts an embodiment of the detection of fetal heart rate with an ultrasound transducer array.

FIG. 3 depicts the operation of the ultrasound transducer array 86 in order to determine fetal heart rate and fetal heart position through the individual operation of a plurality of ultrasound transducers 88. The ultrasound transducers 88 in the ultrasound transducer array 86 are operated to each produce an ultrasound tone signal. In an exemplary embodiment, the ultrasound transducers 88 operate at a 1 MHz carrier signal; however, it will be understood by one of ordinary skill in the art that alternative frequencies of ultrasound carrier signals may be suitable for implementation of embodiments of the device and systems as disclosed herein. The ultrasound transducers 88 of the ultrasound transducer array 86 are operated as a phased array.

In the operation of a phased array ultrasound, each of the ultrasound transducers 88 in the ultrasound transducer array 86 are pulsed separately to create a directional ultrasound beam. By varying the timing of the pulsation of the ultrasound transducers 88, a pattern of constructive interference is set up in a directional beam angle. The manipulation of the sequence and timing of the pulses from each of the ultrasound transducers, the ultrasound beam can be steered electronically through a variety of angles. This creates a search light effect that slices through the tissue or object being examined.

Referring to FIG. 3, two orientations of the angled ultrasound beam are shown in a first orientation 90 and a second orientation 92. In both orientations, all of the ultrasound pulses from each of the ultrasound transducers 88 are directed at the fetal heart when the fetal heart is at a first fetal heart position 94 or a second fetal heart position 96. This diagram demonstrates two advantages of the phased array detection of fetal heart rate.

As the fetus moves within the uterus, the specific location of the fetal heart moves with respect to the ultrasound transducers 88. This is exemplified by the first fetal heart position 94 and the second fetal heart position 96 separated by arrow 98. As the projections of the ultrasound tone signals from the ultrasound transducers 88 sweep through a range of locations represented by angle 100, the ultrasound transducer array 86 is able to both measure the distance traveled by the fetal heart as well as obtain a fetal heart rate when the ultrasound beams of the ultrasound transducer array 86 are focused at the fetal heart. The detection of fetal heart movement is an advantage over previous known ultrasound systems as the detection of fetal heart movement can provide additional information regarding the position and orientation of the fetus during labor as well as the onset and progression of delivery The angling of the ultrasound beams further produce a more focused window of ultrasound coverage at any given point in time as compared to a straightforward projection of the ultrasound signals from each of the ultrasound transducers 88. This increases the signal-noise ratio for the return reflected ultrasound signals from which fetal heart rate is derived. This focused ultrasound beam does not sense other abdominal areas that move independent from the fetal heart and therefore cause sources of doppler noise. One example of a physiological structure that may be avoided by focusing the ultrasound beam as described above is the maternal aorta. The ultrasound signal from the maternal aorta can routinely be stronger than the signal from the fetal heart. Therefore, avoidance of this artifact source improves the overall quality of the signal returned to the ultrasound transducer. This improves the processing of these signals as will be described in further detail herein as well as increases the accuracy and quality of the determination of fetal heart rate.

Figure 4:
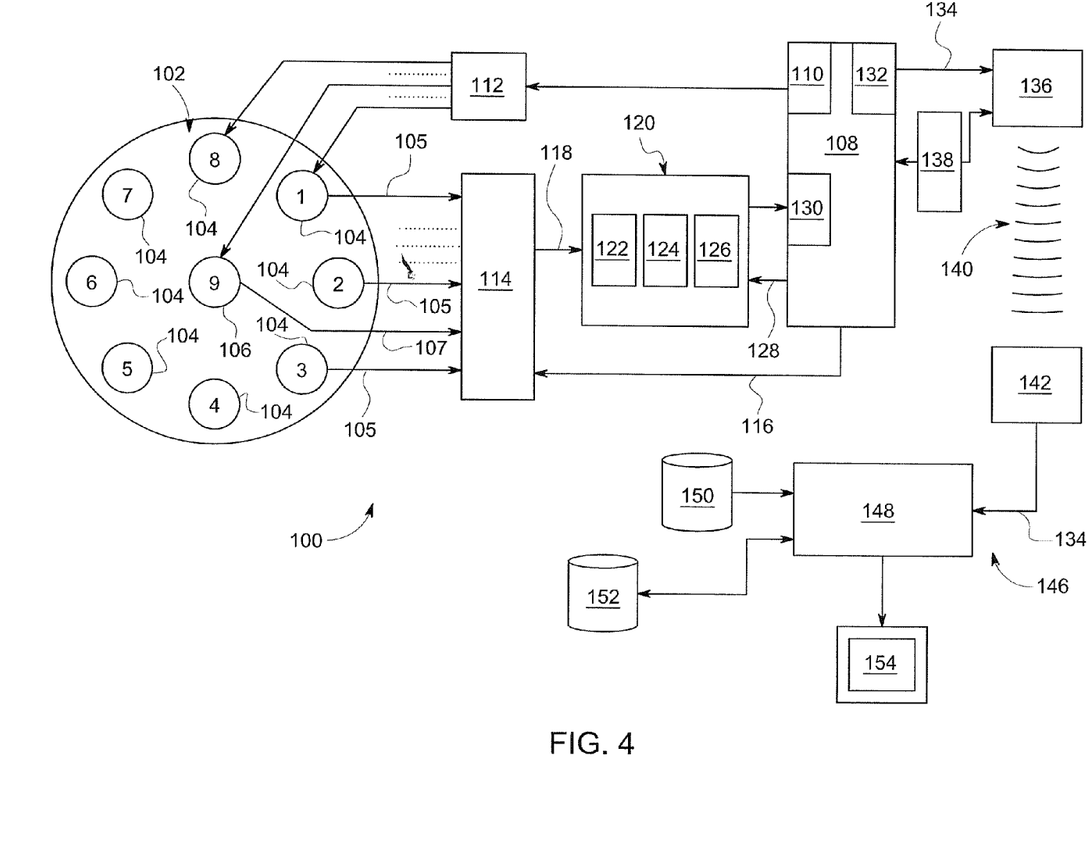
FIG. 4 is a schematic diagram of an embodiment of a system for monitoring a pregnancy.

FIG. 4 is a schematic diagram of an embodiment of a system for monitoring a pregnancy 100. The system includes an ultrasound transducer array 102 that includes a plurality of ultrasound transducers (1-8) 104. While the embodiment of the system 100 depicted shows a plurality of eight ultrasound transducers 104, it is recognized that alternative embodiments may include any number of ultrasound transducers 104. The system IOU further includes at least one additional ultrasound transducer (9) 106. While the embodiment of the system 100 depicted shows a single additional ultrasound transducer 106, it, is recognized that alternative embodiments may include a plurality of additional ultrasound transducers 106.

The system 100 further includes a digital signal processor 108 that performs a variety of operational and control functions as disclosed in further detail herein. In embodiments of the digital signal processor (DSP) 108, the DSP includes memory, exemplarily non-volatile memory upon which is programmed computer readable code that when executed by the DSP 108 causes the DSP to perform the functions and operations as disclosed herein. In an alternative embodiment (not depicted), the DSP 108 is connected to an external source of computer readable memory from which the DSP 108 obtains the computer readable code. The DSP 108 may exemplarily be a C645x DSP available from the Texas Instruments; however, it will be recognized by one of ordinary skill in the art that alternative DSPs may be suitably used in embodiments of the system disclosed herein.

The DSP 108 produces control signals that are sent from general purpose input/output pins (GPIO) 110 of the DSP 108. The control signals from the DSP 108 include a chirp pulse for the uterine activity monitor as disclosed herein and the beam-forming tone pulses for the fetal heart monitoring as disclosed herein. These ultrasound control signals are sent to an amplifier 112. In an exemplary embodiment, the amplifier 112 is a 9-channel amplifier that directs the proper chirp pulse and beam-forming tone pulses to the required ultrasound transducers 104 and additional ultrasound transducer 106. It is understood that the amplifier 112 has been described as a 9-channel amplifier as there are nine ultrasound transducers used in the embodiment of the system disclosed herein. It is further recognized that the number of channels used in the amplifier would be scaled to match the number of ultrasound transducers used in the system.

The ultrasound transducers 104, 106 produce ultrasound signals according to the amplified control signals received from the DSP 108 via the amplifier 112. The ultrasound signals are projected into the mother and fetus as described previously in further detail. Reflected ultrasound signals are returned back to each of the ultrasound transducers 104, 106. The ultrasound transducers 104 receive returned raw fetal heart waveforms. The at least one ultrasound transducer 106 receives returned raw uterine activity waveforms.

The received raw fetal heart waveforms 105 and the raw uterine activity waveforms 107 are provided to a switch 114 that is connected to each of the ultrasound transducers 104, 106. The switch 114 operates between a first condition that communicatively passes the raw fetal heart waveforms 105 from the ultrasound transducers 104 of the ultrasound transducer array 102 and a second condition that communicatively passes the raw uterine activity waveforms 107 from the additional ultrasound transducer 106. The switch 114 operates between the two conditions as directed by a control signal 116 provided to the switch 114 by the DSP 108. In an exemplary embodiment, the control signal 116 from the DSP 108 operates the switch at a frequency of 2 KHz. The raw fetal heart and uterine activity waveforms 118 passed through by the switch 114 are provided to a front end circuitry 120 that processes and conditions the raw fetal heart and uterine activity waveforms. In an exemplary embodiment, the front end circuitry 120 may be an AFE508x device available from Texas Instruments; however, it will be understood by one of ordinary skill in the art that alternative devices may be suitable for use in other embodiments of the system as disclosed herein.

In one embodiment of the front end circuitry 120, the front end circuitry 120 includes an amplifier 122. Amplifier 122 may be a low noise amplifier (LNA) or a programmed gain amplifier (PGA), or any other suitable amplifier or combination of amplifiers as will be recognized by one of ordinary skill in the art. The front end circuitry 102 further includes a filter 124. The filter 124 may exemplarily be a low pass filter or an anti-aliasing filter or any other filter or combination of filters as would be recognized as suitable by one of ordinary skill in the art.

The front end circuitry 120 further includes an analog-to-digital converter (ADC) 126 that converts the analog raw fetal heart and uterine activity waveforms into a digitized format that is receivable by the DSP 108. The DSP 108 provides a control signal 128 to the front end circuitry 120. The control signal 128 facilitates the control the operation to the components of the front end circuitry 120 such as to modify the amplification gain or ADC sample rates. As noted above, the ultrasound signal (and therefore returned reflected ultrasound signals) attenuate as they pass through tissue. In an embodiment, the gain control is further used to compensate for this attenuation.

The DSP 108 receives the digitized raw fetal heart and uterine activity waveforms at an input port which is exemplarily a serial rapid input/output (SRIO) 130.

The DSP 108 processes the received digitized raw fetal heart and uterine activity waveforms for transmission by down converting the raw fetal heart waveform from the high carrier frequency (exemplarily 1 MHz) of the ultrasound transducers 104 to a low carrier frequency (exemplarily 1 KHz). The DSP 108 modulates the raw uterine activity waveform by up converting the waveform from the low frequency band (e.g. 0-100 Hz) of the additional ultrasound transducer 106 to a higher carrier frequency. Exemplarily, the raw uterine activity waveforms are modulated to a 2 KHz carrier frequency. It is understood that other carrier frequencies may be used as dictated by audio band of the wireless transmitter and wireless receiver. In an embodiment using the BTHS module, this audio band may be 20 Hz-8 KHz for mono headsets and 10 Hz-20 KHz for stereo headsets.

The DSP 108 then mixes the modulated ultrasound signals into a combined audio signal. In one embodiment, the combined audio signal is converted into an analog audio signal by a digital-to-analog converter (DAC) 132 to produce an analog audio signal 134. In an alternative embodiment, the combined audio signal is maintained and transmitted as a digital audio signal. In the embodiment of the system 100 depicted in FIG. 4, the DAC 132 is an integral part of the DSP 108; however, it is to be recognized that in alternative embodiments, the DAC is a separate component (not depicted) that is communicatively connected to the DSP 108.

The analog audio signal 134 is provided to a wireless transmitter 136. The wireless transmitter 136 and the DSP 108 both receive electrical energization from a battery 138. In an embodiment, the battery 138 may be a rechargeable battery, alternatively, the battery 138 may be a disposable battery.

The wireless transmitter 136 is exemplarily an RF transmitter, such as, but not limited to a BLUETOOTH wireless transmitter operating according to the BLUETOOTH communication standard. In an alternative embodiment, the wireless transmitter 136 is an infrared or other optical wireless transmission platform. In an exemplary embodiment that implements the wireless transmitter 136 with a BLUETOOTH enabled device that includes a BLUETOOTH headset (BTHS) module that is selected for maximum audio bandwidth. Exemplarily, the BTHS module is a Class 2 module which may be an ARF32 module available from Adeunis or a BTM511 module available from Laird; however, it will be recognized by one of ordinary skill in the art that a variety of BTHS modules, including Class 1 modules, may also be used.

The BTHS module includes headset software profile (HSP) that is well suited for the transmission and receipt of demodulated ultrasound signals.

The wireless transmitter 136 in the embodiment of the system 100, produces an RF signal 140 that is broadcast from the wireless transmitter 136 and received by a compatible wireless receiver 142. It is understood that the wireless receiver 142 is of a compatible and complimentary design and platform with the wireless signals produced by the wireless transmitter 136.

The wireless receiver 142 is either a part of or communicatively connected to a patient monitor 146. The patient monitor 146 includes a controller or microprocessor 148. The microprocessor 148 includes or is communicatively connected to a computer readable medium 150 which is exemplarily flash memory that is programmed with computer readable code that is executed by the microprocessor 148 and causes the microprocessor to perform the operations and functions as disclosed herein. The microprocessor 148 receives the analog audio signal 134 from the wireless receiver 142 and demodulates the analog audio signal 134 in order to extract the raw uterine activity waveforms and the raw fetal heart waveforms. In a non-limiting example, if the raw fetal heart waveforms were down converted to a 1 KHz carrier signal then the analog audio signal 134 is filtered in a pass band between 750 Hz and 1250 Hz. The filtered audio signal is demodulated with a center frequency of 250 Hz in order to extract the raw fetal heart waveforms. If the raw uterine activity waveforms were up converted to 2 KHz, then the analog audio signal 134 is filtered with a pass band between 1950 Hz and 2050 Hz. The filtered audio signal is then demodulated with a center frequency of 50 Hz to obtain the raw uterine activity waveforms.

The microprocessor 148 further processes the raw uterine activity waveforms in order to arrive at an indication of uterine activity that includes, but is not limited to contraction onset, contraction duration, and contraction intensity. These contraction values are obtained from the raw uterine activity waveforms by analyzing the waveform in the manner described above with respect to FIG. 2. As a non-limiting example of the further processing of the raw uterine activity waveforms, the raw uterine activity waveform is filtered with a low pass filter. This resulting filtered waveform is a function of time that is similar to that depicted in FIG. 2B.

The microprocessor 148 further processes the raw fetal heart waveforms in order to obtain an indication of fetal heart rate. As noted above, the use of the phased array technique in obtaining the raw fetal heart waveforms provides improved signal-to-noise ratio which improves the determination of fetal heart rate. The improved fetal-to-noise ratio comes from the focus of the ultrasound beam at the location of the fetal heart to better detect fetal heart movement, rather than current techniques that generally focus an ultrasound beam at the area around the fetal heart and track generalized pulsation within the fetus. Additionally, the microprocessor 148 processes the raw fetal heart waveform to determine any movement in the location of the fetal heart as has been described above with respect to FIG. 3. This indication of fetal heart movement can be used as an indication of fetal location, orientation, or position that is useful information to a clinician in evaluating a mother and fetus during labor and delivery. The microprocessor 148 processes the raw fetal heart waveform to determine the fetal heart rate (FHR) exemplarily includes filtering the raw fetal heart rate waveform with a band pass filter with a pass band between 100 Hz and 300 Hz. An envelope detector is applied to construct an envelope for the filtered raw fetal heart waveforms. An auto correlation technique is applied to obtain the FHR from the waveform envelope.

The microprocessor 148 is further connected to an electronic medical record (EMR) 152 of the patient, which may be located remotely to the microprocessor 148 such as through a communication network. The EMR 152 is used as a record wherein the determinations of uterine activity, fetal heart rate, and fetal heart movement may be stored.

The microprocessor 148 is further connected to a graphical display 154. The microprocessor 148 operates the graphical display 154 such that the graphical 154 presents the obtained indications of fetal heart rate, fetal heart movement, and uterine activity.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An abdominal sonar for use with a pregnant patient, the abdominal sonar comprising:
   an ultrasound transducer array comprising a plurality of ultrasound transducers;
   at least one additional ultrasound transducer;
   a digital signal processor communicatively connected to the plurality of ultrasound transducers of the ultrasound transducer array and communicatively connected to the at least one additional ultrasound transducer, the digital signal processor individually operates the plurality of ultrasound transducers of the ultrasound transducer array to each produce at least one ultrasound tone signal and operates the at least one additional ultrasound transducer to produce at least one ultrasound chirp signal, receives reflected ultrasound signals back from each of the plurality of ultrasound transducers and the at least one additional ultrasound transducer, and down converts the received ultrasound signals from the plurality of ultrasound transducers into a first audio signal in a range of audible frequencies, and modulates the ultrasound signals from the at least one additional ultrasound transducer into a second audio signal in the range of audible frequencies, and the digital signal processor mixes the first audio signal and the second audio signal into a combined audio signal in the range of audible frequencies and
   a wireless transmitter communicatively connected to the digital signal processor, the wireless transmitter receives the combined audio signal from the digital signal processor and broadcasts the received combined audio signal;
   wherein the ultrasound tone signals of the plurality of ultrasound transducers are used to monitor fetal heart rate and the at least one ultrasound chirp signal of the at least one additional ultrasound transducer is used to monitor uterine contractions.

2. The abdominal sonar of claim 1, further comprising:
   front end circuitry communicatively connected between the plurality of ultrasound transducers of the ultrasound transducer array, the at least one additional ultrasound transducer, and the digital signal processor;
   wherein the front end circuitry processes reflected Ultrasound signals before transmitting the ultrasound signals to the digital signal processor.

3. The abdominal sonar of claim 2, wherein the front end circuitry comprises an amplifier, a low pass filter, and an analog to digital converter, that respectively amplify, filter, and digitize the reflected ultrasound signals.

4. The abdominal sonar of claim 2, wherein the ultrasound tone signals from the plurality of ultrasound transducers of the ultrasound transducer array are used by the digital signal processor to monitor fetal heart rate; and
   wherein the at least one ultrasound chirp signal from the at least one additional ultrasound transducer is used by the digital signal processor to monitor uterine contractions.

5. The abdominal sonar of claim 2, further comprising a switch connected to each of the plurality of ultrasound transducers of the ultrasound transducer array and connected to the at least one additional ultrasound transducer, the switch operates between a first condition that communicatively connects the plurality of ultrasound transducers of the ultrasound transducer array to the front end circuitry and a second condition that communicatively connects the at least one additional ultrasound transducer to the front end.

6. The abdominal sonar of claim 1, further comprising:
   a battery electrically connected to the digital signal processor and to the wireless transmitter, the battery provides energization to the digital signal processor and to the wireless transmitter;
   an exterior case at least partially surrounding the ultrasound transducer array, at least one additional ultrasound transducer, the digital signal processor, the wireless transmitter, and the battery; and
   an elastomeric band secured to the exterior case, the elastomeric band configured to removably secure the abdominal sonar to an abdomen of the pregnant patient.

7. A system for monitoring a pregnancy, the system comprising:
   an ultrasound transducer array comprising a plurality of ultrasound transducers;
   at least one additional ultrasound transducer;
   a digital signal processor communicatively connected to the plurality of ultrasound transducers of the ultrasound transducer array and communicatively connected to the at least one additional ultrasound transducer, the digital signal processor individually operates the plurality of ultrasound transducers of the ultrasound transducer array to each produce at least one ultrasound tone signal and the at least one additional ultrasound transducer to produce at least one ultrasound chirp signal, receives raw fetal heart waveforms back from the plurality of ultrasound transducers and down converts the received raw fetal heart waveforms into a first audio signal in a range of audible frequencies, the digital signal processor receives raw uterine activity waveforms back from the at least one additional ultrasound transducer and modulates the raw uterine activity waveform into a second audio signal in the range of audible frequencies, and the digital signal processor mixes the first audio signal and the second audio signal into a combined audio signal in the range of audible frequencies, wherein the range of audible frequencies is between 10 Hz and 20 KHz;
   a wireless transmitter communicatively connected to the digital signal processor, the wireless transmitter receives the combined audio signal from the digital signal processor and broadcasts the received combined audio signal modulated on a radio frequency (RF) signal;

a wireless receiver communicatively connected to the wireless transmitter, such that the wireless receiver receives the broadcast combined audio signal modulated on the RF signal; and a patient monitor communicatively connected to the wireless receiver, the patient monitor extracts the raw fetal heart and uterine activity waveforms from the combined audio signal and processes the raw fetal heart and uterine activity waveforms to obtain an indication of fetal heart rate from the ultrasound tone signal and an indication of uterine activity from the ultrasound chirp signal.

8. The system of claim 7, wherein the wireless transmitter and the wireless receiver operate according to a BLUETOOTH communication standard.

9. The system of claim 7, wherein the patient monitor demodulates the combined audio signal to extract the raw uterine activity waveforms.

10. A system for monitoring a pregnancy, the system comprising:

an ultrasound transducer array comprising a plurality of ultrasound transducers;

at least one additional ultrasound transducer;

a digital signal processor communicatively connected to the plurality of ultrasound transducers of the ultrasound transducer array and communicatively connected to the at least one additional ultrasound transducer, the digital signal processor operates the plurality of ultrasound transducers to produce ultrasound tone signals and operates the at least one additional ultrasound transducer to produce an ultrasound chip signal, the digital signal processor receives reflected ultrasound tone signals back from each of the plurality of ultrasound transducers and a reflected ultrasound chirp signal from the at least one additional ultrasound transducer, and the digital signal processor down converts the received reflected ultrasound tone signals into a first audio signal in a range of audible frequencies, and modulates the received reflected ultrasound chirp signals into a second audio signal in the range of audible frequencies, and the digital signal processor mixes the first audio signal and the second audio signal into a combined audio signal in the range of audible frequencies, wherein the range of audible frequencies is between 10 Hz and 20 KHz;

a wireless transmitter communicatively connected to the digital signal processor, the wireless transmitter receives the combined audio signal from the digital signal processor and broadcasts the combined audio signal;

a wireless receiver communicatively connected to the wireless transmitter, such that the wireless receiver receives the broadcast combined audio signal; and a patient monitor communicatively connected to the wireless receiver, the patient monitor extracts the received reflected ultrasound tone signals and the received reflected ultrasound chirp signal from the combined audio signal and processes the received reflected ultrasound tone signals to obtain an indication of fetal heart rate and processes the received reflected ultrasound chirp signal to obtain an indication of uterine activity.

11. The system of claim 10, wherein the reflected ultrasound tone signals are raw fetal heart waveforms and the reflected ultrasound chirp signal is a raw uterine activity waveform.

12. The system of claim 11, wherein the digital signal processor modulates the raw fetal heart waveforms and the raw uterine activity waveform before combining the raw fetal heart waveforms and the raw uterine activity waveforms into the combined audio signal; and wherein the patient monitor demodulates the combined audio signal to extract the raw fetal heart waveforms and the raw uterine activity waveform.

13. The system of claim 12, wherein the patient monitor obtains the indication of uterine activity by measuring a time delay between echo pulses in the raw uterine activity waveform.

14. The system of claim 10, wherein the audio signal is an analog audio signal, the wireless transmitter is a headset transmitter operating according to a BLUETOOTH communication standard, and the wireless receiver is a headset receiver operating according to the BLUETOOTH communication standard, and the audible frequency range is between 20 Hz and 20 KHz.

15. The abdominal sonar of claim 1, wherein the range of audible frequencies is between 10 Hz and 20 KHz.

* * * * *